_US006063814A_

United States Patent [19]
Chang et al.

[11] Patent Number: 6,063,814
[45] Date of Patent: May 16, 2000

[54] PHORBOL ESTERS AS ANTI-NEOPLASTIC AND WHITE BLOOD CELL ELEVATING AGENTS

[76] Inventors: Richard L. Chang, 107 Konner Ave., Pine Brook, N.J. 07058; Zheng Tao Han, 4 Dongming Road, Zheng Zhou, Henan, China

[21] Appl. No.: 08/837,085

[22] Filed: Apr. 14, 1997

[51] Int. Cl.[7] .................................................. A61K 31/21
[52] U.S. Cl. ............................................................ 514/510
[58] Field of Search ............................................. 514/510

[56] References Cited

PUBLICATIONS

Shih et al., Carcinogenesis (1993), 14(4), 709–12, 1993.

*Primary Examiner*—Jerome D. Goldberg
*Attorney, Agent, or Firm*—Bernard S. Leon

[57] ABSTRACT

Phorbol esters and particularly phorbol-12-myristate-13-acetate (TPA) are described as effective in treating patients with neoplastic diseases such as leukemia as well as in increasing the white blood cell count.

20 Claims, No Drawings

PHORBOL ESTERS AS ANTI-NEOPLASTIC AND WHITE BLOOD CELL ELEVATING AGENTS

BRIEF DESCRIPTION OF THE INVENTION

The invention relates to treating neoplastic disease such as leukemia and increasing the white blood cell counts in patients suffering from neoplastic diseases or undergoing chemotherapy by a method which comprises administering parenterally to patients an effective amount of a phorbol ester of the Formula:

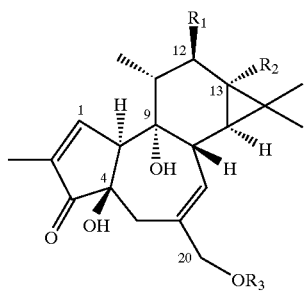

I or isomers thereof wherein $R_1$ and $R_2$ are selected from the group consisting of hydrogen,

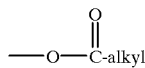

wherein the alkyl group contains 1 to 15 carbon atoms,

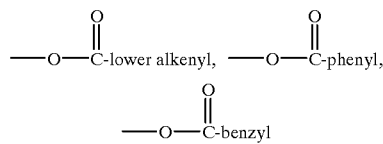

and substituted derivatives thereof. At least one of $R_1$ and $R_2$ is other than hydrogen and $R_3$ is selected from the group consisting of hydrogen and

Preferred are Compounds of the Formula I wherein one of $R_1$ and $R_2$ is selected from the group consisting of

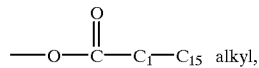

more preferably higher chain alkyl groups, especially decanoate or myristate and the other is —O—C(=O)—lower alkyl and $R_3$ is hydrogen.

Especially preferred is a compound of the formula I where

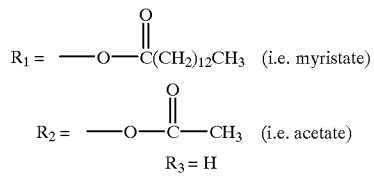

$R_3 = H$ i.e. phorbol-12-myristate-13-acetate or as it is also known 12-O-tetradecanoylphorbol-13-acetate (herein TPA)

The term "lower alkyl" or "lower alkenyl" as used herein shall mean moieties containing 1–7 carbon atoms. In the Compounds of the Formula I, the alkyl or alkenyl groups may be straight or branched chain and preferably contain at least one of $R_1$ or $R_2$, a long chain carbon moiety (decanoate or myristate).

The alkyl, alkenyl, phenyl and benzyl groups may be unsubstituted or substituted with halogen, preferably, chlorine, fluorine or bromine, nitro, amino and similar type radicals.

BACKGROUND OF THE INVENTION

The compounds of the Formula I are generally known to be tumor promoters and as being highly irritant to skin and the mucous membrane.

The preferred exemplar TPA is a biologically active natural compound which can be extracted from croton oil. TPA has been known for many years to be a co-carcinogen or tumor promoter. See Merck Index, 11th Edition, Page 1164 No. 7306. It is also known to be a highly potent irritant to skin and to be harmful if ingested orally. In a product brochure distributed by Chemsyn Science Laboratories of Lenexa, Kansas, TPA is described as an extremely potent mouse skin cancer promoter and as a powerful mitogen in cell cultures. The product brochure warns the user to treat TPA with extreme care. The literature discloses that TPA induces differentiation in the stable human promyelocytic leukemic cell line HL-60. Weinberg, JP (Science 213:655–657, 1981) further discloses that TPA causes differentiation of cells of the human leukemia cell line HL-60 to nondividing macrophage-like cells. These differentiated cells are cytotoxic for tumor cells including current, untreated HL-60 cells in vitro. However, nowhere in the prior art has it been suggested that compounds of the Formula I when delivered parenterally to humans would be effective in treating neoplastic diseases or in raising the white blood cell count, much less without significant unwanted side effects.

Leukemia is a neoplastic disease in which white corpuscle maturation is arrested at a primitive stage of cell development. The disease is characterized by an increased number of leukemic blast cells in the bone marrow and by varying degrees of failure to produce normal hematopoietic cells. The condition may be either acute or chronic. Leukemias are further typically characterized as being lymphocytic or myelocytic. Acute lymphocytic leukemia (ALL) arises in lymphoid tissues and ordinarily first manifests its presence in bone marrow. Acute myelocytic leukemia (AML) arises from bone marrow hematopoietic stem cells or their progeny. The term "acute myelocytic leukemia" subsumes several subtypes of leukemia e.g. myeloblastic leukemia, promyelocytic leukemia and myelomonocytic leukemia.

Chronic myelogenous leukemia is characterized by abnormal proliferation of immature granulocytes, for example, neutrophils, eosinophils and basophils, in the blood, bone marrow, the spleen, liver and sometimes in other tissues. A large portion of chronic myelogenous leukemia patients develop a transformation into a pattern indistinguishable from the acute form of the disease. This change is known as the "blast crises": The present invention is generally suitable for treating leukemias, as well as other neoplastic diseases.

DETAILED DESCRIPTION OF THE INVENTION

Compounds of the Formula I are useful as anti-tumor agents in patients suffering from neoplastic diseases and for raising the white blood cell count in patients suffering from neoplastic diseases such as leukemia and other forms of tumors such as solid tumors and undergoing chemotherapy.

The preferred compound TPA has demonstrated in humans the ability to reduce the abnormal bone marrow profile in patients with AML and other types of leukemia to the point where the patient can be considered to be in remission. Of the patients treated with TPA, all had been diagnosed as having progressed to an acute form of leukemia and the prognosis for a favorable outcome was not very bright. Prior to the administration of TPA, all of the patients had received various forms of conventional chemotherapy including hydroxyurea, busulfan and Ara-C etc without success originally or because of the development of resistance to these drugs. Upon administration of TPA to these refractory patients, clinical remission was achieved in a relatively short time. In addition, during and after the treatment with TPA, there was no bone marrow suppression, infection or bleeding. Many of the patients have been in clinical remission for over six months from the time the treatment with TPA first started.

Additionally, the Compounds of the Formula I can be used to treat patients who are undergoing chemotherapy for the treatment of solid tumors as a method of elevating their white blood cell counts (leukocytes). Chemotherapeutic agents are known to exert toxic effects on certain normal cells in the body. The white blood cells in the body that are responsible for helping the body fight off infections are especially sensitive to chemotherapeutic agents. If these infection fighting cells, (the white blood cells) fall to very low levels in the patient receiving chemotherapy, the patient will become more susceptible to serious infection. TPA has shown the propensity to help speed the rapid recovery of the infection fighting cells, both after and during chemotherapy treatment and therefore TPA is especially useful in reducing the chances of a patient developing serious infections. Often the elevation of the white blood cell count occurs within one day of treatment. The present invention is useful in raising the white blood cell count in patients undergoing chemotherapy for all types of solid tumors such as breast, lung, prostate and colon cancers. TPA helps to maintain adequate levels of white blood cells or infection fighting cells. These cells work by surrounding and destroying bacteria that may have entered the body. TPA, by preventing the number of white blood cells from falling to low levels for long periods of time, lessens the potential for infection, the use of antibiotics and longer hospital stays. Generally by increasing the white blood cell count, the body is reprovided with an important component of its immune system.

Because of the ability to elevate the white blood cell count, the present invention may also be useful in any patient with compromised white blood counts including patients suffering from AIDS.

Also, compounds of the Formula above in animal studies have evidenced the ability to inhibit solid tumor growth in laboratory animals.

Dosage delivery systems, preferably aqueous dosage delivery systems, suitable for parenteral administration of compounds of the Formula I in a pharmaceutical acceptable carrier, can be prepared by dissolving a Compound of the Formula I in an appropriate solvent which is miscible, dispersable or soluble with water, such as an alcohol eg. ethanol, propanol, isopropanol and the like. Other water soluble solvents suitable for the purpose of the present invention include glycols such as propylene glycol or polyethylene glycol, glycerine (glycerol), glycerolformal and the like. There can be added to the dosage forms antimicrobial preservatives such as benzyl alcohol, phenol, cresol (ortho, meta or para or mixtures of the foregoing) and phenylethylalcohol. There can also be added low concentrations of surfactants known to be suitable for intravenous use at low concentrations including Emulphor EL-620, Cremophor EL, Polysorbate 80 (Tween 80) or Polysorbate 20 (Tween 20).

Any solvent or mixtures of solvents and/or preservative and/or surfactant can be selected by the person skilled in the art as the pharmaceutically acceptable carrier in accordance with conventional practices for preparing parenteral dosage formulations. All that is required of a component of the pharmaceutically acceptable carrier to be suitable for the purposes of the present invention is that it be safe when injected into a human; is miscible, dispersible or soluble in water; has no cytotoxicity; and does not diminish the shelf life of the pharmaceutical formulation so that it may be stored.

The compounds of the Formula I in the treatment of neoplastic diseases such as leukemia or for raising white blood cell counts can be administered parenterally (I.V.) in dosage amounts from about 0.001 mg per dose to about 1.5 mg per dose, for about 1–7 times per week for about 1–10 weeks; more preferable from about 0.05 to about 1 mg, 1–7 times per week, for 1–7 weeks; and still more preferably from about 0.1 mg to about 0.6 mg, 1–7 times per week for about 1–7 weeks. The most preferred dosage form is delivered through I.V. infusion and contains 0.1 mg, 0.25 mg or 0.5 mg per dose. The course of therapy preferred is 1–7 weeks with 1 mg being administered over a week in divided doses.

In patients receiving chemotherapy for solid tumors, the most preferred time for administrating a single dose of a compound of the Formula I is about the time the patient is to receive or has just undergone a course of chemotherapy designed to combat the solid tumors.

The precise dosage amount and the duration of administration of a compound of the Formula I will depend on the exigencies of the medical situation and the judgement of the physician treating the patient in accordance with conventional practice among medical professionals. The exact dose will depend upon such factors as the age, weight and condition of the patient, the frequency of administration and the manner in which the patient responds to the treatment.

EXAMPLE I

The following compounds are illustrative of the compounds encompassed by Formula I which are suitable for the purposes of the present invention. These compounds are commercially available.

1) Phorbol 13-Butyrate
2) Phorbol 12-Decanoate
3) Phorbol 13-Decanoate
4) Phorbol 12,13-Diacetate
5) Phorbol 13,20-Diacetate
6) Phorbol 12,13-Dibenzoate
7) Phorbol 12,13-Dibutyrate
8) Phorbol 12,13-Didecanoate
9) Phorbol 12,13-Dihexanoate
10) Phorbol 12,13-Dipropionate
11) Phorbol 12-Myristate
12) Phorbol 13-Myristate
13) Phorbol 12-Myristate-13-Acetate (also known as TPA or PMA)
14) Phorbol 12,13,20-Triacetate
15) 12-Deoxyphorbol 13-Angelate
16) 12-Deoxyphorbol 13-Angelate 20-Acetate
17) 12-Deoxyphorbol 13-Isobutyrate
18) 12-Deoxyphorbol 13-Isobutyrate-20-Acetate
19) 12-Deoxyphorbol 13-Phenylacetate
20) 12-Deoxyphorbol 13-Phenylacetate 20-Acetate
21) 12-Deoxyphorbol 13-Tetradecanoate
22) Phorbol 12-Tigliate 13-Decanoate
23) 12-Deoxyphorbol 13-Acetate
24) Phorbol 12-Acetate
25) Phorbol 13-Acetate

EXAMPLE 2

Formulation Type A 0.10, 0.125, 0.25 or 0.5 mg of TPA was dissolved in 1.3 ml 95–100% U.S.P. ethanol and 0.7 ml saline. Under sterile conditions, TPA was first dissolved in ethanol, then saline was added, mixed vigorously, bacteriologically filtered, and stored in sealed sterile amber vials containing either 0.10 mg/2 ml, 0.125 ml/2 ml or 0.25 mg/2 ml, 0.5 mg/2 ml.

Formulation Type B 0.10, 0.125, 0.25 or 0.5 mg of TPA was dissolved in 0.2 ml of ethanol, 1.2 ml of isopropanol and 0.6 ml saline. Under sterile conditions, TPA was first dissolved in the ethanol and isopropanol, then saline was added, and the mixture was vigorously mixed, bacteriologically filtered and stored in sealed sterile amber vials containing either 0.10 mg/2 ml, 0.125 ml/2 ml or 0.25 mg/2 ml or 0.5 mg/2 ml.

Analytical results showed that there is no chemical change in the TPA solutions stored in the dark at cold temperature for up to one year; also, there is no chemical change in the TPA solutions stored in the dark at room temperature up to two months.

EXAMPLE 3

1. Effect of TPA in a Human Promyelocytic Leukemia Cell Line (HL-60):

HL-60 cells at $2\times10^6$ cells/ml were treated with TPA. The final concentrations of TPA were 10, 20, or 100 ng/ml. The ethanol content was less than 0.01%. After 3 hours of TPA treatment, the cells stopped proliferating and cell aggregation and attachment to the dish were observed. After 48 h of treatment, there were morphological changes. After 4–6 days, morphological and cellular biochemical studies showed that the majority of the cells were induced to differentiate to macrophages in a dose-dependent manner.

EXAMPLE 4

(2) TPA+Low Doses of Ara-C:

The treatment of HL-60 cells with low doses of TPA (20 ng/ml) or Ara-C (100 ng/ml) demonstrated that Ara-C could induce cell differentiation, and TPA at low concentration is a weak cell differentiation-inducing agent. The combination treatment of HL-60 cells with TPA and Ara-C induced the HL-60 cells to differentiate synergistically.

EXAMPLE 5

Effect of TPA in Mice Injected With S180 (Sarcoma 180) Tumor Cells:

Eight groups of Kwen-Ming mice containing 7 mice per group were used in the following experiment. Two groups were untreated and six groups received the drug.

Each Kwen-Ming mouse was injected with $5\times10^6$ S180 cells at the under-arm position. After 24 or 72 h, the animals were given TPA i.p. or locally at the tumor site. The injected doses of TPA were 50, 100 and 200 μg/kg/d for 7 days. The animals were sacrificed 24 hrs after the final TPA treatment and the tumors were weighed to calculate the extent of the tumor growth inhibition. The study showed that the tumor growth was inhibited by 41.7%, 54.8% and 30.4%, respectively, in mice that were injected i.p. with 50, 100 or 200 μg/kg TPA daily for 7 days. The tumor growth was inhibited by 35.5%, 49.3% and 59.2%, respectively, in mice that were injected daily for 7 days with 50, 100 or 200 μg/kg TPA locally at the tumor site in comparison to the control mice. Pathological studies showed that the tumor cells were differentiated after the TPA treatment.

EXAMPLE 6

Effect of TPA in Mice Injected with B16 Tumor Cells:

Four groups of C57 mice were used in the experiment. Each group contained 7 mice and one group was untreated. Each C57 mouse was injected with 0.2 ml of supernatant of a 1:6 w/v homogenate of B16 cells at the under-arm position. On the third day, each treatment group was given TPA i.p. at 50, 100 or 200 μg/kg/d for 8 days. The animals were sacrificed after the treatment, the tumors were weighed, and the rates of inhibition of tumor growth were 40.0%, 59.4% and 32.1%, respectively, which were all statistically different from the control group.

EXAMPLE 7

Effect of TPA on the Peripheral White Blood Cells (WBC) and Hemoglobin (Hb) Counts in S180 Cell-Injected Mice:

S180 cells were injected into mice. On the third day, the mice were given TPA i.p. at 50, 100 or 200 μg/kg/d for 7 days. On the second day after the treatment was completed, blood samples were taken from the tails of the treated mice for WBC and Hb analyses. The WBC counts for the treated groups (50, 100, or 200 ug/kg/d for 7 d) were 16.1±7.4, 18.7±3.0 and 20.7±3.4×$10^9$/L, respectively; the WBC count for the control group was 13.6±1.8×$10^9$/L. The Hb of the treated groups were 136±11, 149±12 and 149±10 g/L, and the Hb of the control group was 134±15 g/L. The results indicate that i.p. injection of TPA could increase the peripheral WBC counts in mice in a dose-dependent manner, whereas the Hb levels were not greatly affected in TPA treated mice when compared to the control mice.

EXAMPLE 8

Study on the Clinical Use of TPA in Humans

1. Dose Ranging Study.

Due to the strong local irritation caused by TPA application, TPA was given to patients by i.v. infusion. TPA solution in a sterile syringe was injected into 200 ml of saline and mixed well for i.v. infusion.

2. The Toxicity and Side Effects of Different TPA Doses Administered Clinically:

(1) TPA given at 1 mg/patient/week:

One mg TPA in solution was mixed well with 200 ml of saline for i.v. infusion which was completed in 1 h at the rate of 16 μg/min. One hour after TPA administration, patients started to have chills which lasted for about 30 min, followed by fever, (the patients' temperature reached 37.5–39.5° C. which lasted for 3–5 h, then returned to normal) with light to heavy perspiration. The above symptoms could be alleviated by giving the patients glucocorticoids. TPA at this dose caused a minority of patients to bleed, several patients suffered for a short period of time difficulty in breathing, and Hb was detected in the urine. However, these side effects were short lived and reversible. The cardiac, hepatic, renal and pulmonary functions were all found to be normal.

(2) TPA given at 0.5 mg/patient×2/week: (two doses a week)

0.5 mg of TPA in solution was mixed well with 200 ml of saline for i.v. infusion which was completed in 1 h at the rate of 8 μg/min. The reactions after administration were similar to that of the 1 mg TPA dosage, but to a lesser extent than the 1 mg dose. The patients tolerated the lower dose more easily. Occasionally, Hb was detected in patients urine. Difficulty in breathing was not observed. The cardiac, hepatic, renal and pulmonary functions were all normal.

(3) TPA given at 0.25 mg/patient×4/week:

0.25 mg of TPA in solution was mixed well with 200 ml of saline for i.v. infusion which was completed in 1 h at the rate of 4 μg/min. After the administration, symptoms such as chills and fever were also observed, but to a much lesser extent than with the higher dosages. No Hb was detected in the urine, and no patient suffered difficulty in breathing. The cardiac, hepatic, renal and pulmonary functions were all normal.

After comparing the above three dosages, 0.25 mg/person×4/week and 0.5 mg/person×2/week are considered to be preferred dosages of TPA.

EXAMPLE 9

The results obtained upon treatment of patients with TPA as presented in tabular form and in subsequent examples.

TABLE 1

Clinical Summary of Clinical Efficacy of TPA in the Five Cases Representing Chronic Myelocytic Leukemia Having Progressed to Acute Myelocytic Leukemia Before TPA Administration (Subjects 1–5) and Five Cases of Other Leukemias (Subjects 6–10)

| Subject No. | Bone marrow Myeloblast and promyelocyte percent of total cells | |
|---|---|---|
| | Before TPA | After TPA |
| 1 | 30 | 2.5 |
| 2 | 36 | 3.0 |
| 3 | 90 | 2.0 |
| 4 | 67.5 | 4.5 |
| 5 | 27.5 | 1.5 |
| 6 | 48 | 3 |
| 7 | 16 | 10 |
| 8 | 80.8 | 17 |
| 9 | (Aplastic anemia) | (TPA terminated) |
| 10 | (9% early in TPA treatment) | 0 |

TABLE 2

Clinical Summary of TPA induced White Blood Cell Changes (WBC) in Patients with Solid Tumors Undergoing Chemotherapy

| Subject No. | WBC (x $10^9$/liter) | |
|---|---|---|
| | Before TPA | Peak after TPA |
| 11 | 0.7 | 6.8 |
| 12 | 3.0 | 4.5 |
| 13 | 0.9 | 2.5 |
| 14 | 3.8 | 8.0 |
| 15 | 2.4 | 7.1 |
| 16 | 2.4 | 5.2 |
| 17 | 2.0 | 4.4 |
| 18 | 2.4 | 4.0 |
| 19 | 2.9 | 5.1 |
| 20 | 0.7 | 2.7 |
| 21 | 1.1 | 1.5 |
| 22 | 1.9 | 7.6 |
| 23 | 2.3 | 3.9 |
| 24 | 1.1 | 5.3 |
| 25 | 2.1 | 6.4 |
| 26 | 3.6 | 5.6 |

EXAMPLE 10

In the subjects identified as (1) through (5) below, chronic myelocytic leukemia had progressed to acute myelocytic leukemia before treatment with TPA.

Subject No. (1) T.S., male, 32, patient No. 28879. Blood profile before TPA treatment: Hb: 28 g/L; WBC: $1.0 \times 10^9$/L, platelet: $135 \times 10^9$/L. Bone marrow profile before TPA treatment: myeloblast+promyelocyte: 30%. TPA treatment: 1 mg/week (0.25 mg administered four times) for two weeks. Blood profile after treatment: Hb: 86 g/L; WBC: $2.8 \times 10^9$/L, platelet: $283 \times 10^9$/L. Bone marrow profile after TPA treatment: myeloblast+promyelocyte: 2.5%.

Subject No. (2) C.J., male, 30, patient No. 29926. Diagnosis: chronic myelocytic leukemia became acute myelocytic leukemia before treatment. Blood profile before TPA treatment: Hb: 94 g/L; WBC: $9.8 \times 10^9$/L, platelet: $63 \times 10^9$/L. Spleen: 3 cm below the rib cage. Bone marrow profile before TPA treatment: myeloblast+promyelocyte: 36%. TPA treatment: 1 mg/week for 5 weeks. Blood profile after treatment: Hb: 104 g/L; WBC: $4.9 \times 10^9$/L, platelet: $80 \times 10^9$/L. Spleen: 0.5 cm below the rib cage. Bone marrow profile after TPA treatment: myeloblast+promyelocyte: 3%.

Subject No. (3) Z.K., male, 42, patient No. 18102. Diagnosis: chronic myelocytic leukemia became acute myelocytic leukemia before treatment. Blood profile before TPA treatment: Hb: 70 g/L; WBC: $27.5 \times 10^9$/L, platelet: $21 \times 10^9$/L. Bone marrow profile before TPA treatment: myeloblast+promyelocyte: 90%. TPA treatment: 1 mg/week for 7 weeks. Blood profile after treatment: Hb: 96 g/L; WBC: $22 \times 10^9$/L, platelet: $70 \times 10^9$/L. Bone marrow profile after TPA treatment: myeloblast+promyelocyte: 2%.

Subject No. (4) W.F. male, 25, patient No. 21315. Diagnosis: chronic myelocytic leukemia became acute myelocytic leukemia before treatment. Blood profile before TPA treatment: Hb: 87 g/L; WBC: $19 \times 10^9$/L, platelet: $150 \times 10^9$/L. Bone marrow profile before TPA treatment: myeloblast+promyelocyte: 67.5%. TPA treatment: 1 mg/week for 7 weeks. Blood profile after treatment: Hb: 45 g/L; WBC: $53.5 \times 10^9$/L, platelet: $210 \times 10^9$/L. Bone marrow profile after TPA treatment: myeloblast+promyelocyte: 4.5%.

Subject No. (5) D.H., male, 38, patient No. 23965. Diagnosis: chronic myelocytic leukemia progressed to acute myelocytic leukemia. Blood profile before TPA treatment: Hb: 84 g/L; WBC: $36.6 \times 10^9$/L, platelet: $290 \times 10^9$/L. Bone marrow profile before TPA treatment: myeloblast+promyelocyte: 27.5%. TPA treatment: 1 mg/week for 2 weeks. Blood profile after treatment: Hb: 84 g/L; WBC: $27.3 \times 10^9$/L, platelet: $170 \times 10^9$/L. Bone marrow profile after TPA treatment: myeloblast+promyelocyte: 1.5%.

All the above patients had received various regimens of chemotherapy prior to the TPA treatment, including hydroxyurea, busulfan, and Ara-C, etc. but none was effective at the start of TPA treatment. Before the administration of TPA, patients received injection of $6 \times 10^5$ units of vitamin $D_3$ ($VD_3$)/person for 2 days; after the TPA administration, patients received i.v. infusion of 40 mg of Ara-C/d×3. After the treatment, the patients all achieved clinical remission in bone marrow parameters in a short time. In addition, during and after the treatment, there was no bone marrow suppression, nor infection or bleeding. These patients have been in clinical remission for over 6 months.

EXAMPLE 11

Other Types of Leukemia:

Subject No. (6) Y.P., male, 57. Diagnosed as AML-M3. Symptoms began in January, 1995. Blood profile: Hb:60 g/L, WBC: $0.4 \times 10^9$/L, platelet: $40 \times 10^9$/L. Bone marrow profile: myeloblast+promyelocyte: 48%. The TPA treatment period was 1 mg/week for three weeks, and $6 \times 10^5$ units $VD_3$/d×3 were injected prior to the treatment. After the first treatment period, blood profile: Hb:118 g/L, WBC: $4.1 \times 10^9$/L, platelet: $80 \times 10^9$/L. Bone marrow profile: myeloblast+promyelocyte: 3%, which met the standard for AML-M3 remission. The patient has been in remission after treatment for at least 6 months.

Subject No. (7) M.W., male, 67. Diagnosis: MDS-REAB accompanied by an increased number of monocytes. Four months of oral VP16 administration failed to produce results. The patient started to receive a combination treatment of 1,25-$(OH)_2$ $VD_3$ +TPA+low dose Ara-C. TPA dosage: 0.25–0.5 mg (1 mg per week) for eleven weeks. Blood profile before TPA treatment: Hb: 36 g/L; WBC: $4.0 \times 10^9$/L, platelet: $29 \times 10^9$/L. Myeloblast: 2%, Promyelocyte: 4%, Myelocyte: 3%, Neutrophil: 60%, Lymphocyte: 25%, Monocyte 6%. Bone marrow profile before treatment: active in proliferation, myeloblast: 8%, promyelocyte: 8%. Spleen: 3 cm below the rib cage. After the treatment: Spleen: 0.5 cm below the rib cage. Blood profile: Hb: 42 g/L; WBC: $10.2 \times 10^9$/L, platelet: $34 \times 10^9$/L. Neutrophil: 80%, Lymphocyte: 19%, Monocyte 1%. Promyelocytes were not detected. Bone marrow profile: active in proliferation, myeloblast: 4%, promyelocyte: 6%.

Subject No. (8) L.Q., male, 36. Diagnosis: AML-M3. Treatment with retinoic acid (RA) at 80 mg/day×50 was not successful. Blood profile before the treatment with TPA: Hb: 45 g/L, WBC: $1.0 \times 10^9$/L, platelet: $35 \times 10^9$/L. Bone marrow profile: very active in proliferation, myeloblast+promyelocyte: 80.8%. Blood profile after the TPA treatment: Hb: 66 g/L, WBC: $2.2 \times 10^9$/L, platelet: $223 \times 10^9$/L. Bone marrow profile: active in proliferation, myeloblast+promyelocyte: 17%.

Subject No. (9) Z.H., female, 21. Diagnosis: bone marrow suppression after receiving chemotherapy for chronic myelocytic leukemia, secondary aplastic anemia. The patient was treated with busulfanum (Busulfan) for 3 months. Blood profile before TPA treatment: Hb: 43 g/L; WBC: $1.6 \times 10^9$/L, platelet: $26 \times 10^9$/L. Bone marrow profile: aplastic anemia. TPA dosage: 0.25 mg×2. Blood profile after the TPA treatment: Hb: 32 g/L, WBC: $1.9 \times 10^9$/L, platelet: $57 \times 10^9$/L. Due to severe anemia, the TPA treatment was terminated.

Subject No. (10) L.N., female, 26. Diagnosis: CML. The patient had been treated with chemotherapy using the combination of homoharringtomine and Ara-C. Blood profile before TPA treatment: Hb: 98 g/L; WBC: $2.0 \times 10^9$/L, platelet: $10^2 \times 10^9$/L. 0.25 mg TPA administered to the patient once. Blood profile after treatment: Hb: 96 g/L; WBC: $2.0 \times 10^9$/L, platelet: $112 \times 10^9$/L. On the second day after TPA treatment: myeloblast+promyelocyte: 4%, myelocyte 5%. On the fifth day after the TPA treatment, these types of blood cells completely disappeared.

EXAMPLE 12

Patients undergoing chemotherapy for the treatment of solid tumors.

Subject No. (11) L.X., female, 50. Diagnosis: malignant lymphoma. The patient had received adramycin, vincristine, and hormonal treatment. The blood cell counts were decreased to: Hb: 78 g/L, WBC: $0.7 \times 10^9$/L, platelet: $245 \times 10^9$/L. 0.25 mg TPA was administered to the patient 4 times. The blood cell counts improved to: Hb: 76 g/L, WBC: $6.8 \times 10^9$/L, platelet: $331 \times 10^9$/L. Chemotherapy was then continued for 5 more days, and followed by one dose of 0.5 mg TPA. The WBC count was maintained at $3.0 \times 10^9$/L. The patient is still receiving treatment.

Subject No. (12) Y.G., female, 45. Diagnosis: brain tumor. Blood profile after chemotherapy was: Hb: 119 g/L, WBC: $3.0 \times 10^9$/L, platelet: $399 \times 10^9$/L. 0.25 mg TPA was given to the patient once. On the day after the TPA treatment, the blood profile was Hb: 123 g/L, WBC: $4.5 \times 10^9$/L, platelet: $436 \times 10^9$/L. The patient received further chemotherapy.

Subject No. (13) G.F., male, 60. Diagnosis: lung cancer. After chemotherapy, his blood cell counts were decreased to: Hb: 76 g/L, WBC: $0.9 \times 10^9$/L, platelet: $100 \times 10^9$/L. 0.25 mg TPA was given to the patient twice. On the day after the TPA treatment, Hb: 74 g/L, WBC: $2.5 \times 10^9$/L, platelet: $110 \times 10^9$/L. The patient is still receiving treatment.

Subject No. (14) Z.R., female, 44. Diagnosis: breast cancer. The WBC after chemotherapy was $3.8 \times 10^9$/L. 0.25 mg of TPA was given to the patient once. The WBC on the day after the TPA treatment was $8.0 \times 10^9$/L.

Subject No. (15) C.Z., female, 75. Diagnosis: Esophageal Cancer. Surgery was performed, followed by chemotherapy using cisplatin, 5-fluorouracil. Blood profile (before TPA): WBC: $2.4 \times 10^9$/L; neutrophil: 83%, lymphocyte: 17%; platelet: $150 \times 10^9$/L; RBC: $3.43 \times 10^{12}$/L; Hb: 107 g/L. TPA dosage: 0.25 mg. Blood profile (one day after TPA): WBC: $7.1 \times 10^9$/L; neutrophil: 94%; lymphocyte: 6%; platelet: $77 \times 10^9$/L; RBC: $3.33 \times 10^{12}$/L; Hb: 109 g/L. Blood profile (4 days after TPA): WBC: $4.4 \times 10^9$/L; neutrophil: 97%; lymphocyte: 3%; platelet: $105 \times 10^9$/L; RBC: $3.36 \times 10^{12}$/L, Hb: 112 g/L. Symptoms after TPA: Chill, fever, local irritation and slight headache. The cardiac, hepatic, renal and pulmonary functions were normal.

Subject No. (16) X.H., female, 60. Diagnosis: Esophageal Cancer. Surgery was performed, followed by chemotherapy using VP16, MTX, MMC and cisplatin. TPA dose: 0.25 mg. Blood profile (before TPA): WBC: $2.4 \times 10^9$/L; neutrophil: 67%; lymphocyte: 23%; platelet: $101 \times 10^9$/L; RBC: $3.45 \times 10^{12}$/L; Hb: 114 g/L. Blood profile (one day after TPA): WBC: $5.2 \times 10^9$/L; neutrophil: 87%; lymphocyte: 13%; platelet $60 \times 10^9$/L; RBC: $3.76 \times 10^{12}$/L; Hb: 122 g/L. Blood profile (2 days after TPA administration). WBC: $4.5 \times 10^9$/L; neutrophil 80%; lymphocyte: 20%; platelet: $64 \times 10^9$/L; RBC: $2.99 \times 10^{12}$/L; Hb: 109 g/L. Symptoms after TPA: chills, fever, local irritation, cardiac, hepatic, renal and pulmonary were normal.

Subject No. (17) Y.Z., female, 37. Diagnosis: breast cancer. Surgery was performed, followed by chemotherapy using CTX, MTX, and 5-FU. TPA dose: 0.25 mg×2 (Second dose was 4 days after 1st dose). Blood profile (before TPA): WBC: $2.0 \times 10^9$/L; neutrophil: 85%; lymphocyte: 15%; platelet: $106 \times 10^9$/L; RBC: $3.24 \times 10^{12}$/L; Hb: 107 g/L. Blood profile (3 days after first TPA dose): WBC: $2.9 \times 10^9$/L; neutrophil 83%; lymphocyte: 17%; platelet: $122 \times 10^9$/L; RBC: $3.36 \times 10^{12}$/L; Hb: 107 g/L. Blood profile (2 days after second TPA dose): WBC: $3.8 \times 10^9$/L; neutrophil: 84%; lymphocyte: 16%; platelet: $84 \times 10^9$/L; RBC: $3.47 \times 10^{12}$/L. Blood profile (4 days after second TPA dose): WBC: $4.4 \times 10^9$/L; neutrophil: 86%; lymphocyte: 14%; platelet $193 \times 10^9$/L; RBC: $3.49 \times 10^{12}$/L; Hb: 112 g/L. Symptoms after TPA: patient started to have chills which lasted for 2 hrs followed by fever, temperature reached 38° C. which lasted 4 hrs and local irritation. The cardiac, hepatic, renal and pulmonary functions were normal.

Subject No. (18) H.P., male, 56. Diagnosis: Colon cancer. Surgery was performed, followed by chemotherapy using Cisplatin, VP16, and 5-FU. TPA dose: 0.25 mg×2 (2nd TPA dose was administered 24 hrs after 1st TPA dose). Blood profile (before TPA): WBC: $2.4 \times 10^9$/L; neutrophil: 63%; lymphocyte: 37%; platelet: $208 \times 10^9$/L; RBC: $4.0 \times 10^{12}$; Hb: 104 g/L. Blood profile (one day after 2nd TPA dose): WBC: $4.0 \times 10^9$/L; neutrophil: 60%; lymphocyte: 40%; platelet: $198 \times 10^9$/L; RBC: $4.1 \times 10^{12}$; Hb: 112 g/L. Symptoms after TPA: chills, fever, local irritation. Cardiac hepatic, renal and pulmonary functions were normal.

Subject No. (19) Z.T., male, 66. Diagnosis: lung cancer metastasized to adrenal gland. Surgery was performed, followed by chemotherapy using MMC, VCR, and CTX. TPA dosage: 0.25 mg×2 (2nd TPA dose was administered 24 hrs after 1st TPA dose). Blood profile (before TPA): WBC: $2.9 \times 10^9$/L; neutrophil: 76%; lymphocyte: 24%; platelet: $227 \times 10^9$/L; RBC: $3.33 \times 10^{12}$/L; Hb: 100 g/L. Blood profile (one day after second TPA dose): WBC: $5.1 \times 10^9$/L; neutrophil: 82%; lymphocyte: 18%; platelet: N/A; RBC: N/A; Hb: 93 g/L. Blood profile (2 days after 2nd TPA dose): WBC: $5.0 \times 10^9$/L; neutrophil: 80%; lymphocyte: 20%; platelet: N/A; RBC: $3.25 \times 10^{12}$; Hb: 101 g/L. Symptoms after TPA: chills, fever, local irritation. Cardiac, hepatic renal and pulmonary functions were normal.

Subject No. (20) J.Z., male, 68. Diagnosis: esophageal cancer metastasized to liver, lung and brain. The patient received chemotherapy using Taxol, cisplatin, 5-FU and Semustial. Total TPA dosage: 2mg. Blood profile (before TPA): WBC: $0.7 \times 10^9$/L; neutrophil: 29%; lymphocyte: 71%; platelet: N/A; RBC: $2.82 \times 10^{12}$/L; Hb: 87 g/L. TPA treatment schedule. On the first and third day, 0.25 mg was given and on the 5th, 7th and 9th day 0.5 mg of TPA was given. Blood profile (at day 2): WBC: $0.9 \times 10^9$/L; neutrophil: 66%; lymphocyte: 34%; platelet: $82 \times 10^9$/L; RBC: $2.17 \times 10^{12}$/L; Hb: 72 g/L. Blood profile (at day 4): WBC: $1.1 \times 10^9$/L; neutrophil: 91%; lymphocyte: 9%; platelet: $39 \times 10^9$/L; RBC: $2.09 \times 10^{12}$/L; Hb: 58 g/L. Blood profile (at day 6): WBC: $1.9 \times 10^9$/L; neutrophil: 95%; lymphocyte: 5%; platelet: $43 \times 10^9$/L; RBC: $1.9 \times 10^{12}$; Hb: 70 g/L. Blood profile (at day 8): WBC: $2.3 \times 10^9$/L; neutrophil: 91%; lymphocyte: 9%; platelet: $90 \times 10^9$/L; RBC: $1.71 \times 10^{12}$/L; Hb: 61 g/L. Blood profile (at 11th day): WBC: $2.7 \times 10^9$/L; neutrophil: 85%; lymphocyte: 15%; platelet: $37.6 \times 10^9$/L; RBC: $2.91 \times 10^{12}$/L; Hb: 61 g/L. Blood profile (at day 13): WBC: $1.9 \times 10^9$/L; neutrophil: 90%; lymphocyte: 10%; platelet: $32 \times 10^9$/L; RBC: $1.73 \times 10^{12}$/L; Hb: 57 g/L. Symptoms after TPA: Chills at 5th day which lasted about one hour. Cardiac, hepatic, renal and pulmonary functions were normal.

Subject No. (21) D.Y., female, 32. Diagnosis: lymphoma metastasized to bone marrow. The patient was treated with chemotherapy using CTX, ADM, and VCR prior to TPA treatment. TPA dosage: 0.25 mg. TPA treatment schedule: 0.25 mg of TPA was administered on days 1 and 2. 0.5 mg of TPA was administered on days 3, 5, 6 and 8. Blood profile (before TPA): WBC: $1.1 \times 10^9$/L; neutrophil: 73%; lymphocyte: 27%; platelet: $144 \times 10^9$/L; RBC: $4.15 \times 10^{12}$/L; Hb: 142 g/L. Blood profile (at day 2): WBC: $0.6 \times 10^9$/L; neutrophil: N/A; lymphocyte: N/A; platelet: $69 \times 10^9$/L; RBC: $4.15 \times 10^{12}$/L: Hb: 117 g/L. Blood profile (at day 4): WBC: $0.6 \times 10^9$/L; neutrophil: 28%; lymphocyte: 72%; platelet: $68 \times 10^9$/L; RBC: $3.95 \times 10^{12}$/L; Hb: 109 g/L. Blood profile (at day 7): WBC: $0.8 \times 10^9$/L; neutrophil: 88%; lymphocyte: 12%; platelet: $60 \times 10^9$/L; RBC: $4.22 \times 10^{12}$/L; Hb: 110 g/L. Blood profile (at day 9): WBC: $1.5 \times 10^9$/L; neutrophil: 80%; lymphocyte: 2%; platelet: $69 \times 10^9$/L; RBC: $4.02 \times 10^{12}$/L; Hb: 112 g/L. Symptoms after TPA: No chills and fever, only local irritation. Cardiac, hepatic, renal and pulmonary functions same as before TPA treatment. Since this patient's lymphoma cells had metastasized to the bone marrow, she required a high dose of TPA (2.5 mg) and a longer treatment time (9 days) in order to induce a very low level of WBC.

Subject No. (22) X.Y., female, 34. Diagnosis: Nasopharyngeal carcinoma metastasized to neck lymph node. The patient was treated with chemotherapy using 5-FU, ADM, and MMX prior to treatment with TPA. Blood profile after chemotherapy (but before TPA treatment): WBC: $1.9 \times 10^9$/L; neutrophil: 89%; lymphocyte: 11%; Hb: 118 g/L. Blood profile (one day after administration of 0.25 mg): WBC $1.8 \times 10^9$/L; neutrophil: 79%; lymphocyte: 21%; Hb: 116 g/L. Blood profile (three days after TPA administration): WBC. $2.9 \times 10^9$/L; neutrophil: 73%; lymphocyte: 27%; Hb: 123 g/L. Blood profile (7 days after TPA administration): WBC: $7.6 \times 10^9$/L; neutrophil: 82%; lymphocyte: 18%; Hb: 118 g/L. Symptoms after TPA: Chills, fever (39.2° C.) continued for 4 hrs. Liver, kidney, heart and lung were functioning normally.

Subject No. (23) J.H., male, 55. Diagnosis: stomach (cardia) cancer, reoccurred after prior surgery. The patient had received 5-FU and MMC. before treatment with TPA. Blood profile (before TPA administration): WBC: $2.3 \times 10^9$/L; neutrophil: 52%; lymphocyte: 48%; Hb: 144 g/L. Blood profile (one day after 0.25 mg TPA administration): WBC: $1.9 \times 10^9$/L; neutrophil: 53%; lymphocyte: 47%; Hb: 123 g/L. Blood profile (four days after TPA): WBC: $3.9 \times 10^9$/L; neutrophil: 44%; lymphocyte: 56%; Hb: 129 g/L. Blood profile (seven days after TPA): WBC: $3.7 \times 10^9$/L; neutrophil: 48%; lymphocyte: 52%; Hb: 138 g/L. Symptoms after TPA: No chills. Low fever (37.8° C.). Functions of liver, kidney, heart and lung were normal.

Subject No. (24) W.L., male, 62. Diagnosis: multiple myeloma. The patient had received VCR, ADM, and DXM before treatment with TPA. Blood profile (before TPA administration): WBC: 1.1×10⁹/L; neutrophil: 73%; lymphocyte: 27%; Hb: 112 g/L. Blood profile (one day after administration of 0.25 mg TPA): WBC: 5.3×10⁹/L; neutrophil: 60%; lymphocyte: 40%; Hb: 139 g/L. Symptoms after TPA: No chills, no fever, no local irritation. Liver, kidney, heart and lung were functioning normally.

Subject No. (25) T.L., female, 42. Diagnosis: breast cancer. The patient received chemotherapy treatment using CTX, MMC, and 5-FU. Blood profile (before TPA): WBC: 2.1×10⁹/L; neutrophil: 72%; lymphocyte: 28%; Hb: 126 g/L. Blood profile (one day after administration of 0.25 mg of TPA): WBC: 6.4×10⁹/L; neutrophil: 90%; lymphocyte: 10%; Hb: 126 g/L. Symptoms after TPA administration: No chills, no fever. Injection site was red, swollen in appearance and painful probably caused by the infusion needle. The symptoms disappeared the second day after they appeared. Liver, kidney, heart and lung were functioning normally.

Subject No. (26) Q.W., male, 56. Diagnosis: esophageal cancer which had metastasized to the liver after surgery. The patient had received chemotherapy using cisplatin and taxol. TPA dosage: 0.25 mg. Blood profile (before TPA administration): WBC: 3.6×10⁹/L; neutrophil: 80%; lymphocyte: 20%; Hb: 124 g/L. Blood profile (one day after TPA administration): WBC: 4.2×10⁹/L; neutrophil: 83%; lymphocyte: 17%; Hb: 120 g/L. Blood profile (2 days after TPA): WBC: 5.6×10⁹/L; neutrophil: 81%; lymphocyte: 19%; Hb: 116 g/L. Symptoms after TPA administration: temperature reached 39° C. which lasted 3 hr. Stomach ache and diarrhea (which disappeared soon after). The cardiac, hepatic, renal and pulmonary functions were normal.

Abbreviations

VP16, Etoposide; MMC, Mitomycin C; MTX, Methotrexate; 5FU, 5-fluorouracil; CTX, Cyclophosphamide; CP, Cisplatin; VD₃, vitamin D₃; MDS-RAEB, Myelodysplastic syndrome-refractory anemia with excessor blasst; Ara-C, cytarabine; AML, Acute myelocytic leukemia; Ml, AML without differentiation; M2, AML with maturation; M3, Acute promyelocytic leukemia; M4, Acute myelomonocytic leukemia; M5, Acute monocytic leukemia; RT, Retention time; WBC, White blood cells; Hb, Hemoglobin.

What is claimed is:

1. A method of treating leukemia which comprises administrating parenterally to patients afflicted with leukemia, an effective amount of a compound of the Formula

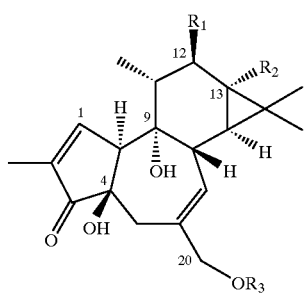

I or isomers thereof
wherein $R_1$ and $R_2$ are selected from the group consisting of hydrogen,

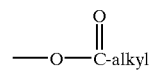

wherein the alkyl group contains 1–15 carbon atoms,

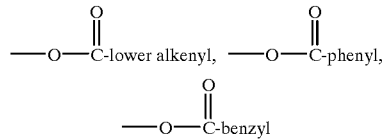

or substituted derivatives thereof, at least one of $R_1$ and $R_2$ is other than hydrogen and $R_3$ as selected from the group consisting of hydrogen and

2. A method as in claim 1 wherein the effective amount is from about 0.001 mg to about 1.5 mg per single dose administered 1–7 times per week for 1–7 weeks.

3. A method as in claim 2 wherein the effective amount is from about 0.05 mg to about 1 mg. per dose delivered 1–7 times per week for 1–7 weeks.

4. A method as in claim 3 wherein the effective amount is from about 0.05 mg to about 0.6 mg. per dose.

5. A method as in claim 4 wherein the effective amount is 1 mg. per week for 1–7 weeks.

6. A method as in claim 5 wherein the leukemia is myelocytic.

7. A method as in claim 6 wherein at least one of $R_1$ or $R_2$ is decanoate or myristate.

8. A method as in claim 7 wherein one of $R_1$ and $R_2$ is

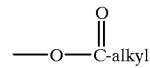

wherein the alkyl group contains 1–15 carbon atoms and the other is

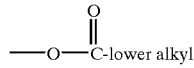

and $R_3$ is hydrogen.

9. A method as in claim 6 wherein the leukemia is acute myelocytic leukemia.

10. A method as in claim 9 wherein in the compound of the Formula I, $R_1$ is

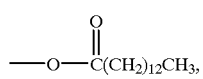

$R_2$ is

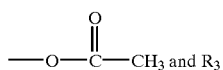

and $R_3$ is hydrogen.

11. A pharmaceutical composition suitable for parenteral administration to humans which comprises from about 0.05 mg, to about 1.5 mg, of a Compound of the Formula

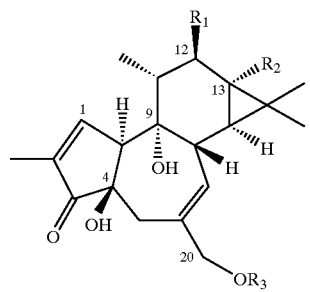

or isomers thereof wherein $R_1$ and $R_2$ are selected from the group consisting of hydrogen

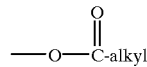

wherein the alkyl group contains 1–15 carbon atoms,

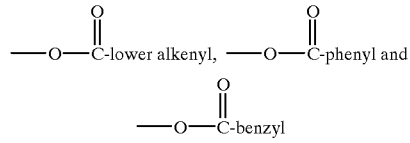

and substituted derivatives thereof, and at least one of $R_1$ and $R_2$ is other than hydrogen and $R_3$ is selected from the group consisting of hydrogen and

and a pharmaceutically acceptable carrier for a Compound of the Formula I.

12. A composition in claim 11 wherein the carrier is an aqueous medium.

13. A composition as in claim 12 which contains from about 0.05 mg to 1.0 mg of a Compound of the Formula I.

14. A composition as in claim 12 which contains from about 0.05 mg to 0.6 mg.

15. A composition as in claim 13 wherein one of $R_1$ or $R_2$ is

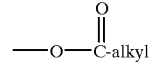

and the other is

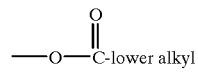

and $R_3$ is hydrogen.

16. A composition as in claim 14 wherein $R_1$ is

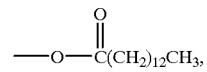

$R_2$ is

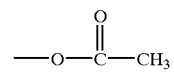

and $R_3$ is hydrogen.

17. A composition as in claim 11 wherein at least one of $R_1$ or $R_2$ is decanoate or myristate.

18. A composition as in claim 11 wherein the Compound of the Formula I is present in dosage amounts of 0.10 mg, 0.25 mg or 0.50 mg.

19. A composition as in claim 18 wherein the dosage form for parenteral administration is an ampoule.

20. A composition as in claim 19 wherein the Compound of the Formula I is phorbol-12-myristate-13-acetate.

* * * * *